(12) United States Patent
Matsuzaki et al.

(10) Patent No.: US 7,300,788 B2
(45) Date of Patent: Nov. 27, 2007

(54) METHOD FOR GENOTYPING POLYMORPHISMS IN HUMANS

(75) Inventors: Hajime Matsuzaki, Palo Alto, CA (US); Rui Mei, Santa Clara, CA (US); Mei-Mei Shen, Cupertino, CA (US); Giulia C. Kennedy, San Francisco, CA (US)

(73) Assignee: Affymetrix, Inc., Santa Clara, CA (US)

( * ) Notice: Subject to any disclaimer, the term of this patent is extended or adjusted under 35 U.S.C. 154(b) by 293 days.

(21) Appl. No.: 10/681,773

(22) Filed: Oct. 7, 2003

(65) Prior Publication Data

US 2004/0146890 A1    Jul. 29, 2004

Related U.S. Application Data

(60) Provisional application No. 60/417,190, filed on Oct. 8, 2002, provisional application No. 60/470,475, filed on May 14, 2003.

(51) Int. Cl.
*C12M 1/34* (2006.01)
*C12M 3/00* (2006.01)
*C07H 21/04* (2006.01)
*C12Q 1/68* (2006.01)

(52) U.S. Cl. ............ 435/287.2; 536/23.1; 536/24.3; 435/91.1

(58) Field of Classification Search ............ None
See application file for complete search history.

(56) References Cited

U.S. PATENT DOCUMENTS 5,900,481 A * 5/1999 Lough et al. ............ 536/55.3
6,812,339 B1 * 11/2004 Venter et al. ............ 536/24.31

OTHER PUBLICATIONS

Hacker et al; Gut, 1997, vol. 40, pp. 623-627.*
Pennisi, Science, 1998; 281 (5384):1787-1789.*
Malhotra et al; Am. J. Of Psychiatry, vol. 161, pp. 780-796, May 2004.*
dbSNP build history.*
Affymetrix GeneChip Human Mapping 10K array (product Data Sheet, 2003; pp. 1-4).*
Carrasquillo, Minerva M., et al., Genome-wide association study and mouse model identify interaction between RET and EDNRB pathways in Hirschsprung disease, Nature Genetics, Oct. 2002, pp. 237-244, vol. 32, Nature Publishing Group, New York, NY, USA.
Dalma-Weiszhausz, Dennise D., et al., Single nucleotide polymorphisms and their characterization with oligonucleotide microarrays, Psychiartic Genetics, 2002, pp. 97-107, vol. 12, No. 2, Lippincott Williams & Wilkins, Philadelphia, PA, USA.
Dong, Shoulian, et al., Flexible Use of High-Density Oligonucleotide Arrays for Single-Nucleotide Polymorphism Discovery and Validation, Genome Research, 2001, pp. 1418-1424, vol. 11, Cold Spring Harbor Laboratory Press, USA.
Dumur, Caterine I., et al., Genome-wide detection of LOH in prostate cancer using human SNP microarray technology, Genomics, 2003, pp. 260-269, vol. 81, Academic Press, USA.
Fan, Jian-Bing, et al., Paternal Origins of Complete Hydatidiform Moles Proven by Whole Genome Single-Nucleotide Polymorphism Haploytyping, Genomics, Jan. 2002, pp. 58-62, vol. 79, No. 1, Academic Press, USA.
Garcia, Christine Kim, et al., Sequence Diversity in Genes of Lipid Metabolism, Genome Research, 2001, pp. 1043-1052, vol. 11, Cold Spring Harbor Laboratory Press, USA.
Guo, Qingbin M., DNA Microarray and cancer, Current Opinion in Oncology, 2003, pp. 36-43, vol. 15, Lippincott Williams & Wilkins, Philadelphia, PA, USA.
Halushka, Marc K., et al., Patterns of single-nucleotide polymorphisms in candidate genes for blood-pressure homeostasis, Nature Genetics, Jul. 1999, pp. 239-247, vol. 22, Nature America, Inc., USA.
Lindblad-Toh, Kerstin, et al., Loss-of-heterozgosity analysis of small-cell lung carcinomas using single-nucleotide polymorphism arrays, Nature Biotechnology, Sep. 2000, pp. 1001-1005, vol. 18, Nature Publishing Group, New York, NY, USA.
Lindblad-Toh, Kerstin, et al., Large-scale discovery and genotyping of single-nucleotide polymorphisms in the mouse, Nature Genetics, Apr. 2000, pp. 381-386, vol. 24, Nature America, Inc., USA.
Lindroos, Katarina, et al., Minisequencing on oligonucleotide microarrays: comparison of immobilisation chemistries, Nucleic Acids Research, 2001, pp. e69 (1-7), vol. 29, No. 13, Oxford University Press, UK.
Mei, Rui, et al., Genome-wide Detection of Allelic Imbalance Using Human SNPs and High-density DNA Arrays, Genome Research, 2000, pp. 1126-1137, vol. 10, No. 8, Cold Spring Harbor Laboratory Press, USA.

(Continued)

*Primary Examiner*—Jehanne Sitton
(74) *Attorney, Agent, or Firm*—Sandra E. Wells

(57) ABSTRACT

The invention provides nucleic acid sequences that are complementary, in one embodiment, to a wide variety of human polymorphisms. The invention provides the sequences in such a way as to make them available for a variety of analyses including genotyping a large number of SNPs in parallel. The invention also provides a collection of human SNPs that is useful for genetic analysis within and across populations. As such, the invention relatesd to diverse fields impacted by the nature of genetics, including biology, medicine, and medical diagnostics.

4 Claims, No Drawings

OTHER PUBLICATIONS

Schubert, Elizabeth L., et al., Single Nucleotide Polymorphism Array Analysis of Flow-Sorted Epithelial cells from Frozen Versus Fixed Tissues for Whole Genome Analysis of Allelic Loss in Breast Cancer, American Journal of Pathology, Jan. 2002, pp. 73-79, vol. 160, No. 1, American Society for Investigative Patholoy, USA.

Warrington, Janet A., et al., New Developments in High-Throughput Resequencing and Variation Detection Using High Density Microarrays, Human Mutation, 2002, pp. 402-409, vol. 19, No. 4, Wiley-Liss, Inc., USA.

Wilson, S.G., et al., Comparison of Genome Screens for Two Independent Cohorts Provides Replication of Suggestive Linkage of Bone Mineral Density to 3p21 and 1p36, American Journal of Human Genetics, 2003, pp. 144-155, vol. 72, No. 1, American Socity of Human Genetics, USA.

Zhou, Wei, Mapping genetic alterations in tumors with single nucleotide polymorphisms, Current Opinion in Oncology, 2003, pp. 50-54, vol. 15, No. 1, Lippincott Williams & Wilkins, Inc, Philadelphia, PA, USA.

Rubenstein, K, The Current State of the Biochip Business, Drug & Market Development, Nov. 1999, pp. 392-396, vol. 10, No. 11, Drug & Market Development Publications, USA.

* cited by examiner

METHOD FOR GENOTYPING POLYMORPHISMS IN HUMANS

RELATED APPLICTIONS

The present application claims priority to U.S. Provisional Application Nos. 60/417,190 filed Oct. 8, 2002 and 60/470,475 filed May 14, 2003 the disclosures of which are each incorporated herein by reference in their entireties.

FIELD OF THE INVENTION

The present invention provides pools of nucleic acid sequences and arrays of nucleic acid sequences that are useful for genotyping polymorphisms in nucleic acid samples derived from humans. The invention also provides a collection of SNPs that may be amplified reproducibly and genotyped in parallel using a single assay. The invention relates to diverse fields, including genetics, genomics, biology, population biology, medicine, and medical diagnostics.

REFERENCE TO SEQUENCE LISTING

The Sequence Listing submitted on compact disk is hereby incorporated by reference.
The file on the disk is named 3522.2seqlist.txt, the file is 17.0 MB and the date of creation is Oct. 6, 2003.

BACKGROUND

The past years have seen a dynamic change in the ability of science to comprehend vast amounts of data. Pioneering technologies such as nucleic acid arrays allow scientists to delve into the world of genetics in far greater detail than ever before. Exploration of genomic DNA has long been a dream of the scientific community. Held within the complex structures of genomic DNA lies the potential to identify, diagnose, or treat diseases like cancer, Alzheimer disease or alcoholism. Exploitation of genomic information from plants and animals may also provide answers to the world's food distribution problems.

Recent efforts in the scientific community, such as the publication of the draft sequence of the human genome in February 2001, have changed the dream of genome exploration into a reality. Genome-wide assays, however, must contend with the complexity of genomes; the human genome for example is estimated to have a complexity of $3 \times 10^9$ base pairs. Novel methods of sample preparation and sample analysis that reduce complexity may provide for the fast and cost effective exploration of complex samples of nucleic acids, particularly genomic DNA.

Single nucleotide polymorphisms (SNPs) have emerged as the marker of choice for genome wide association studies and genetic linkage studies. Building SNP maps of the genome will provide the framework for new studies to identify the underlying genetic basis of complex diseases such as cancer, mental illness and diabetes. Due to the wide ranging applications of SNPs there is still a need for the development of robust, flexible, cost-effective technology platforms that allow for scoring genotypes in large numbers of samples.

All documents, i.e., publications and patent applications, cited in this disclosure, including the foregoing, are incorporated by reference herein in their entireties for all purposes to the same extent as if each of the individual documents were specifically and individually indicated to be so incorporated by reference herein in its entirety.

SUMMARY OF THE INVENTION

The invention provides nucleic acid sequences that are complementary to particular regions of the human genome that are known or predicted to contain single nucleotide polymorphisms (SNPs). The invention further provides a collection of SNPs that are useful for performing analysis of the human genome. For example, in one embodiment the invention comprises an array comprising any 10 or more, 100 or more, 1000 or more, 10,000 or more, 100,000 or more, or 1,000,000 or more nucleic acid probes containing 9 or more consecutive nucleotides from the sequences listed in SEQ ID NOS: 1-124,031, or the perfect match, perfect mismatch, antisense match or antisense mismatch thereof. In a preferred embodiment the array comprises each of the sequences listed in SEQ ID NOS 1-124,031, each probe being a different 25 nucleotide sequence from the sequence listing. In a further embodiment, the invention comprises the use of any of the above arrays or fragments disclosed in SEQ ID NOS 1-124,031 to: monitor loss of heterozygosity; identify imprinted genes; genotype polymorphisms; determine allele frequencies in a population, characterize biallelic markers; produce genetic maps; detect linkage disequilibrium, determine allele frequencies, do association studies, analyze genetic variation, to identify markers linked to a phenotype or, compare genotypes between different individuals or populations. In a further embodiment the invention comprises a method of analysis comprising hybridizing one or more pools of nucleic acids to two or more of the fragments disclosed in SEQ ID NOS 1-124,031 and detecting said hybridization. In a further embodiment the invention comprises the use of any one or more of the fragments disclosed in SEQ ID NOS 1-124,031 as a primer for PCR.

DETAILED DESCRIPTION OF THE INVENTION a) General

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), *Lehninger, Principles of Biochemistry* $3^{rd}$ Ed., W.H. Freeman Pub., New York, N.Y. and Berg et al. (2002) *Biochemistry*, $5^{th}$ Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252, 743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US01/04285, which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring, and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Serial Nos. 60/319,253, 10/013,598, and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, e.g., *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. The sample may be amplified on the array. See, for example, U.S. Pat. No. 6,300,070 which is incorporated herein by reference.

Other suitable amplification methods include the ligase chain reaction (LCR) (e.g., Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA*, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. No. 5,413,909, 5,861,245) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 5,242,794, 5,494,810, 4,988,617 and in U.S. Ser. No. 09/854,317, each of which is incorporated herein by reference.

Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. Ser. Nos. 09/916,135, 09/920,491, 09/910,292, and 10/013,598. Additional methods of using a genotyping array are disclosed, for example, in U.S. patent application Ser. Nos. 10/442,021, 10/650,332, 10/316,629, 10/316,517, 10,264,945, 10/321, 741, 60/496,539, and 60/453,930.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* ($2^{nd}$ Ed. Cold Spring Harbor, N.Y., 1989); Berger and Kimmel *Methods in Enzymology*, Vol. 152, *Guide to Molecular Cloning Techniques* (Academic Press, Inc., San Diego, Calif., 1987); Young and Davism, *P.N.A.S,* 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 60/364,731 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800, 992, 5,834,758; 5,856,092, 5,902,723, 5,936,324, 5,981, 956, 6,025,601, 6,090,555, 6,141,096, 6,185,030, 6,201, 639; 6,218,803; and 6,225,625, in U.S. Ser. No. 60/364,731 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and *Ouelette and Bzevanis Bioinformatics: A Practical Guide for Analysis of Gene and Proteins* (Wiley & Sons, Inc., $2^{nd}$ ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in U.S. Ser. Nos. 10/063,559 (United States Publication No. US20020183936), 60/349,546, 60/376,003, 60/394,574 and 60/403,381.

Each of the references, patents and patent applications cited in the specification is incorporated be reference in its entirety for all purposes.

B. Definitions

Massive Parallel Screening: The phrase "massively parallel screening" refers to the simultaneous screening of from about 100, 1000, 10,000 or 100,000 to 1000, 10,000, 100, 000, 1,000,000 or 3,000,000 or more different nucleic acid hybridizations.

Probe: As used herein a "probe" is defined as a nucleic acid capable of binding to a target nucleic acid of complementary sequence through one or more types of chemical bonds, usually through complementary base pairing, usually through hydrogen bond formation. As used herein, a probe may include natural (i.e. A, G, U, C, or T) or modified bases (7-deazaguanosine, inosine, etc.). In addition, a linkage other than a phosphodiester bond may join the bases in probes. Modifications in probes may be used to improve or alter hybridization properties. Thus, probes may be peptide nucleic acids in which the constituent bases are joined by peptide bonds rather than phosphodiester linkages. Other modifications may also be used, for example, methylation or inclusion of a label or dye.

Perfect match: The term "match," "perfect match," "perfect match probe" or "perfect match control" refers to a nucleic acid that has a sequence that is designed to be perfectly complementary to a particular target sequence or portion thereof. For example, if the target sequence is 5'-GATTGCATA-3' the perfect complement is 5'-TATG-CAATC-3'. Where the target sequence is longer than the probe the probe is typically perfectly complementary to a portion (subsequence) of the target sequence. For example, if the target sequence is a fragment that is 800 bases, the perfect match probe may be perfectly complementary to a 25 base region of the target. A perfect match (PM) probe can be a "test probe", a "normalization control" probe, an expression level control probe and the like. A perfect match control or perfect match is, however, distinguished from a "mismatch" or "mismatch probe."

Mismatch: The term "mismatch," "mismatch control" or "mismatch probe" refers to a nucleic acid whose sequence is deliberately designed not to be perfectly complementary to a particular target sequence. As a non-limiting example, for each mismatch (MM) control in a high-density probe array there typically exists a corresponding perfect match (PM) probe that is perfectly complementary to the same particular target sequence. The mismatch may comprise one or more bases. While the mismatch(es) may be located anywhere in the mismatch probe, terminal mismatches are less desirable because a terminal mismatch is less likely to prevent hybridization of the target sequence. In a particularly preferred embodiment, the mismatch is located at the center of the probe, for example if the probe is 25 bases the mismatch position is position 13, also termed the central position, such that the mismatch is most likely to destabilize the duplex with the target sequence under the test hybridization conditions. A homo-mismatch substitutes an adenine (A) for a thymine (T) and vice versa and a guanine (G) for a cytosine (C) and vice versa. For example, if the target sequence was: 5'-AGGTCCA-3', a probe designed with a single homo-mismatch at the central, or fourth position, would result in the following sequence: 3'-TCCTGGT-5', the PM probe would be 3'-TCCAGGT-5'.

DNA Library—as used herein the term "genomic library" or "genomic DNA library" refers to a collection of cloned DNA molecules consisting of fragments of the entire genome (genomic library) or of DNA copies of all the mRNA produced by a cell type (cDNA library) inserted into a suitable cloning vector.

Nucleic acids according to the present invention may include any polymer or oligomer of pyrimidine and purine bases, preferably cytosine, thymine, and uracil, and adenine and guanine, respectively. (See Albert L. Lehninger, *Principles of Biochemistry*, at 793-800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 20 nucleotides in length, but may be up to 50, 100, 1000, or 5000 nucleotides long or a compound that specifically hybridizes to a polynucleotide. Polynucleotides of the present invention include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety.) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

A genome is all the genetic material of an organism. In some instances, the term genome may refer to the chromosomal DNA. Genome may be multichromosomal such that the DNA is cellularly distributed among a plurality of individual chromosomes. For example, in human there are 22 pairs of chromosomes plus a gender associated XX or XY pair. DNA derived from the genetic material in the chromosomes of a particular organism is genomic DNA. The term genome may also refer to genetic materials from organisms that do not have chromosomal structure. In addition, the term genome may refer to mitochondria DNA. A genomic library is a collection of DNA fragments representing the whole or a portion of a genome. Frequently, a genomic library is a collection of clones made from a set of randomly generated, sometimes overlapping DNA fragments representing the entire genome or a portion of the genome of an organism.

The term "chromosome" refers to the heredity-bearing gene carrier of a cell which is derived from chromatin and which comprises DNA and protein components (especially histones). The conventional internationally recognized individual human genome chromosome numbering system is employed herein. The size of an individual chromosome can vary from one type to another within a given multi-chromosomal genome and from one genome to another. In the case of the human genome, the entire DNA mass of a given chromosome is usually greater than about 100,000,000 bp. For example, the size of the entire human genome is about $3 \times 10^9$ bp. The largest chromosome, chromosome no. 1, contains about $2.4 \times 10^8$ bp while the smallest chromosome, chromosome no. 22, contains about $5.3 \times 10^7$ bp.

A "chromosomal region" is a portion of a chromosome. The actual physical size or extent of any individual chromosomal region can vary greatly. The term "region" is not necessarily definitive of a particular one or more genes because a region need not take into specific account the particular coding segments (exons) of an individual gene.

An allele refers to one specific form of a genetic sequence (such as a gene) within a cell, an individual or within a population, the specific form differing from other forms of the same gene in the sequence of at least one, and frequently more than one, variant sites within the sequence of the gene. The sequences at these variant sites that differ between different alleles are termed "variances", "polymorphisms", or "mutations". At each autosomal specific chromosomal location or "locus" an individual possesses two alleles, one inherited from one parent and one from the other parent, for example one from the mother and one from the father. An individual is "heterozygous" at a locus if it has two different alleles at that locus. An individual is "homozygous" at a locus if it has two identical alleles at that locus.

Polymorphism refers to the occurrence of two or more genetically determined alternative sequences or alleles in a population. A polymorphic marker or site is the locus at which divergence occurs. Preferred markers have at least two alleles, each occurring at a frequency of preferably greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. A diallelic polymorphism has two forms. A triallelic polymorphism has three forms. A polymorphism between two nucleic acids can occur naturally, or be caused by exposure to or contact with chemicals, enzymes, or other agents, or exposure to agents that cause damage to nucleic acids, for example, ultraviolet radiation, mutagens or carcinogens.

Single nucleotide polymorphisms (SNPs) are positions at which two alternative bases occur at appreciable frequency (>1%) in a given population. SNPs are the most common type of human genetic variation. A polymorphic site is frequently preceded by and followed by highly conserved sequences (e.g., sequences that vary in less than 1/100 or 1/1000 members of the populations).

A SNP may arise due to substitution of one nucleotide for another at the polymorphic site. A transition is the replacement of one purine by another purine or one pyrimidine by another pyrimidine. A transversion is the replacement of a purine by a pyrimidine or vice versa. SNPs can also arise from a deletion of a nucleotide or an insertion of a nucleotide relative to a reference allele.

The term genotyping refers to the determination of the genetic information an individual carries at one or more positions in the genome. For example, genotyping may comprise the determination of which allele or alleles an individual carries for a single SNP or the determination of which allele or alleles an individual carries for a plurality of SNPs. For example, a particular nucleotide in a genome may be an A in some individuals and a C in other individuals. Those individuals who have an A at the position have the A allele and those who have a C have the C allele. In a diploid organism the individual will have two copies of the sequence containing the polymorphic position so the individual may have an A allele and a C allele or alternatively two copies of the A allele or two copies of the C allele. Those individuals who have two copies of the C allele are homozygous for the C allele, those individuals who have two copies of the A allele are homozygous for the C allele, and those individuals who have one copy of each allele are heterozygous. The array may be designed to distinguish between each of these three possible outcomes. A polymorphic location may have two or more possible alleles and the array may be designed to distinguish between all possible combinations.

A genetic map is a map that presents the order of specific sequences on a chromosome. A genetic map expresses the positions of genes relative to each othere without a physical anchor on the chromosome. The distance between markers is typically determined by the frequency of recombination, which is related to the relative distance between markers. Genetic map distances are typically expressed as recombination units or centimorgans (cM). The physical map gives the position of a marker and its distance from other genes or markers on the same chromosome in base pairs and related to given positions along the chromosome. See, *Color Atlas of Genetics*, Ed. Passarge, Thieme, New York, N.Y. (2001), which is incorporated by reference. Genetic variation refers to variation in the sequence of the same region between two or more individuals.

Normal cells that are heterozygous at one or more loci may give rise to tumor cells that are homozygous at those loci. This loss of heterozygosity may result from structural deletion of normal genes or loss of the chromosome carrying the normal gene, mitotic recombination between normal and mutant genes, followed by formation of daughter cells homozygous for deleted or inactivated (mutant) genes; or loss of the chromosome with the normal gene and duplication of the chromosome with the deleted or inactivated (mutant) gene.

Linkage disequilibrium or allelic association means the preferential association of a particular allele or genetic marker with a specific allele, or genetic marker at a nearby chromosomal location more frequently than expected by chance for any particular allele frequency in the population. For example, if locus X has alleles a and b, which occur at equal frequency, and linked locus Y has alleles c and d, which occur at equal frequency, one would expect the combination ac to occur at a frequency of 0.25. If ac occurs more frequently, then alleles a and c are in linkage disequilibrium. Linkage disequilibrium may result, for example, because the regions are physically close, from natural selection of certain combination of alleles or because an allele has been introduced into a population too recently to have reached equilibrium with linked alleles. A marker in linkage disequilibrium can be particularly useful in detecting susceptibility to disease (or other phenotype) notwithstanding that the marker does not cause the disease. For example, a marker (X) that is not itself a causative element of a disease, but which is in linkage disequilibrium with a gene (including regulatory sequences) (Y) that is a causative element of a phenotype, can be detected to indicate susceptibility to the disease in circumstances in which the gene Y may not have been identified or may not be readily detectable.

The term "target sequence", "target nucleic acid" or "target" refers to a nucleic acid of interest. The target sequence may or may not be of biological significance. Typically, though not always, it is the significance of the target sequence which is being studied in a particular experiment. As non-limiting examples, target sequences may include regions of genomic DNA which are believed to contain one or more polymorphic sites, DNA encoding or believed to encode genes or portions of genes of known or unknown function, DNA encoding or believed to encode proteins or portions of proteins of known or unknown function, DNA encoding or believed to encode regulatory regions such as promoter sequences, splicing signals, polyadenylation signals, etc. In many embodiments a collection of target sequences comprising one or more SNPs from Table 1 is assayed. One of skill in the art will recognize that genomic DNA in humans and related primates is double stranded. Each of the SNPs in Table 1 thus represents two complementary strands. The polymorphic position represents a base pair, for example, if the allele on one strand is a G, the allele on the opposite strand is a C. In addition to the polymorphic position, there is also sequence that is upstream and downstream, or 5' of and 3' of the SNP position. The at least 50 bases upstream and at least 50 bases downstream of the SNP is preferably the same for each allele of the SNP for each SNP in Table 1.

The SNPs of Table 1 were selected based on shared characteristics that allow two or more target sequences comprising SNPs from Table 1 to be amplified reproducibly in the same amplification reaction. The SNPs of Table 1 are found on fragments between 300 and 1000 base pairs when human genomic DNA is digested with XbaI may be interrogated in a single assay. A single array may interrogate more than 2, 100, 1000, 5,000 or more SNPs from Table 1. The array may interrogate for the presence or absence of different alleles in the SNPs of Table 1.

Target sequences may be interrogated by hybridization to an array. The array may be specially designed to interrogate one or more selected target sequence. The array may contain a collection of probes that are designed to hybridize to a region of the target sequence or its complement. Different probe sequences are located at spatially addressable locations on the array. For genotyping a single polymorphic site probes that match the sequence of each allele may be included. At least one perfect match probe, which is exactly complementary to the polymorphic base and to a region surrounding the polymorphic base, may be included for each allele. In a preferred embodiment the array comprises probes that include 12 bases on either side of the SNP. Multiple perfect match probes may be included as well as mismatch probes.

The methods may be combined with other methods of genome analysis and complexity reduction. Other methods of complexity reduction include, for example, AFLP, see U.S. Pat. No. 6,045,994, which is incorporated herein by reference, and arbitrarily primed-PCR (AP-PCR) see McClelland and Welsh, in *PCR Primer: A laboratory Manual*, (1995) eds. C. Dieffenbach and G. Dveksler, Cold Spring Harbor Lab Press, for example, at p 203, which is incorporated herein by reference in its entirety. Additional methods of sample preparation and techniques for reducing the complexity of a nucleic sample are described in Dong et al., *Genome Research* 11, 1418 (2001), in U.S. Pat. Nos. 6,361,947, 6,391,592, 6,458,530 and U.S. Patent Application Nos. 20030039069, Ser. Nos. 09/916,135, 09/920,491, 09/910,292 and 10/264,945, which are incorporated herein by reference in their entireties.

An "array" comprises a support, preferably solid, with nucleic acid probes attached to the support. Preferred arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 5,800,992, 6,040,193, 5,424,186 and Fodor et al., *Science*, 251:767-777 (1991), each of which is incorporated by reference in its entirety for all purposes.

Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as fiber optics, glass or any other appropriate substrate. (See U.S. Pat. Nos. 5,770,358, 5,789,162, 5,708,153, 6,040,193 and 5,800,992, which are hereby incorporated by reference in their entirety for all purposes.)

Arrays may be packaged in such a manner as to allow for diagnostic use or can be an all-inclusive device; e.g., U.S. Pat. Nos. 5,856,174 and 5,922,591 incorporated in their entirety by reference for all purposes. Preferred arrays are commercially available from Affymetrix (Santa Clara, Calif.) under the brand name GeneChip® and are directed to a variety of purposes, including genotyping and gene expression monitoring for a variety of eukaryotic and prokaryotic species.

Hybridization probes are oligonucleotides capable of binding in a base-specific manner to a complementary strand of nucleic acid. Such probes include peptide nucleic acids, as described in Nielsen et al., *Science* 254, 1497-1500 (1991), and other nucleic acid analogs and nucleic acid mimetics. See U.S. patent application Ser. No. 08/630,427.

Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see, for example, Sambrook et al. which is hereby incorporated by reference in its entirety for all purposes above.

An individual is not limited to a human being, but may also include other organisms including but not limited to mammals, plants, fungi, bacteria or cells derived from any of the above.

C. Interrogation of Selected Human SNPs

SEQ ID NOS 1-124,031, are disclosed. Each of the sequences is complementary to one allele of a human SNP listed in Table 1 (Table 1 lists two alleles for each SNP) and 12 bases upstream and downstream of the SNP. Each sequence corresponds to and represents at least three additional nucleic acid sequences included in the invention. For example, if the first nucleic acid sequence listed in SEQ ID NOS 1-124,031 is: 5'-cggatcgcg-3', which is the sense match probe (complementary to one strand of the target sequence), the additional sequences included in the invention which are represented by this nucleic acid sequence are, for example:
5'-cggaacgcg-3'=sense mismatch probe (mismatch base underlined)
5'-cgcgatccg-3'=antisense match probe
5'-cgcgttccg-3'=antisense mismatch probe (mismatch base underlined)

Accordingly, for each nucleic acid sequence listed in SEQ ID NOS 1-124,031, this disclosure includes the corresponding sense mismatch, antisense match, and antisense mismatch probes. The position of the mismatch is preferably located at the central position of the probe, for example, for a probe of 25 nucleotides, the mismatch position would be position 13. In another embodiment the mismatch position may be located anywhere in the nucleic acid sequence and may comprise one or more bases. Generally the sequences correspond to SNPs present in Table 1 and the sequence immediately surrounding the SNP, for example 12-25 bases upstream and downstream of the SNP. The SNPs are preferably biallelic but may be triallelic and the probes in a preferred embodiment are used to distinguish between different alleles of a SNP. Frequency of SNPs vary between populations so a SNP that is biallelic in one population may not be polymorphic in another population or may be represented by different alleles. The sequences in SEQ ID NOS 1-124,031 correspond to the perfect match probes for 12,450 SNPs listed in Table 1. In one embodiment, for each SNP there are 10 perfect match probes that are each 25 nucleotides. Some probes were omitted from the sequence listing because they were duplicates of other probes. The probes correspond to perfect match probes for each allele for each SNP. In general there are 5 perfect match probes for each allele which vary according to the position of the polymorphic base. In some probes the polymorphic base is in the center of the 25 nucleotide probe, corresponding to the 13$^{th}$ nucleotide from the 5' end. In the other probes the polymorphic base is shifted from the center, or 0, position. The polymorphic position may be shifted toward the 5' end of the probe or toward the 3' end of the probe. For example, in SEQ ID NOS 1-5 the polymorphic base corresponds to the A at position 17, (+4), in SEQ ID NO 1; the polymorphic base is shifted to position 15, (+2) in SEQ ID NO 2; to position 14, (+1), in SEQ ID NO 3, it is in position 13, (0), in SEQ ID NO 4 and in position 12, (−1), in SEQ ID NO 5. SEQ ID NOS 6-10 are identical to SEQ ID NOs 1-5 except the polymorphic base corresponds to a G. The polymorphic base may also be shifted further from the 0 position, for example, it may be located from −10 to +10. In a preferred embodiment the mismatch position remains at position 13.

The present invention includes: the sequences listed in SEQ ID NOS 1-124,031 and the complement of these sequences as well as mismatch probes, longer nucleotide sequences which include the nucleic acid sequences listed in SEQ ID NOS 1-124,031 and the complement of these sequences and sub-sequences greater than 9 nucleotides in length of the target nucleic acid sequences listed in SEQ ID NOS 1-124,031 and the complement of these sequences.

The nucleic acid sequences listed in SEQ ID NOS 1-124, 031 correspond to regions of the human genome containing SNPs. SNPs represented by SEQ ID NOS 1-124,031 are identified in Table 1. Each of the numbers in Table 1 is a reference SNP ID or "rs" ID that identifies a SNP in the NCBI (National Center for Biotechnology Information) SNP database (dbSNP). A reference SNP ID, or 'rs' ID is an identification tag assigned by NCBI to SNPs that appear to be unique in the database. The rs ID number, or tag, is assigned at submission. For example, 1000018A, refers to the A allele of a SNP at position 62126003 of chromosome 2. The observed alleles are A and T. A search of the dbSNP database for rs1000018 provides available information about the SNP.

SNPs were selected from the publicly available database of human SNPs. The selected SNPs are from the group of SNPs that are present on XbaI fragments of 300 to 1000 base pairs. A computer system was used to predict fragments that would result when the human genome is digested with XbaI. Those fragments in a selected size range, 300-1000 base pairs, were selected for further analysis. Of those fragments those that carried a SNP were selected as potential target sequences. SNPs were selected from these potential target sequences and the selected SNPs are represented by SEQ ID NOS 1-124,031 and in Table 1. In some embodiments the present invention provides a pool of unique nucleotide sequences complementary to SNPs and sequence surrounding SNPs which alone, or in combinations of 2 or more, 10 or more, 100 or more, 1,000 or more, 10,000 or more or 100,000 or more can be used for a variety of applications.

In one embodiment, the present invention provides for a pool of unique nucleotide sequences which are complementary to Human SNPs and sequence surrounding SNPs formed into a high density array of probes suitable for array based massive parallel gene expression. Array based methods for SNP analysis and genotyping are disclosed and discussed in detail in U.S. Pat. Nos. 6,361,947 and 6,368, 799 which are incorporated herein by reference for all purposes. Generally those methods of SNP analysis involve: (1) providing a pool of target nucleic acids comprising one or more target sequence(s), (2) amplifying a collection of target sequences, (3) hybridizing the amplified nucleic acid sample to a high density array of probes, and (4) detecting the hybridized nucleic acids and determining the presence or absence of one or more alleles for one or more SNPs.

The development of Very Large Scale Immobilized Polymer Synthesis or VLSIPS™ technology has provided methods for making very large arrays of nucleic acid probes in very small arrays. See U.S. Pat. No. 5,143,854 and PCT Nos. WO 90/15070 and 92/10092, and Fodor et al., *Science*, 251:767-77 (1991), each of which is incorporated herein by reference. U.S. Pat. No. 5,800,992 and 6,040,138 describe methods for making arrays of nucleic acid probes that can be used to detect the presence of a nucleic acid containing a specific nucleotide sequence. Methods of forming high-density arrays of nucleic acids, peptides and other polymer sequences with a minimal number of synthetic steps are known. The nucleic acid array can be synthesized on a solid substrate by a variety of methods, including, but not limited to, light-directed chemical coupling, and mechanically directed coupling.

In one embodiment probes are present on the array so that each SNP is represented by a collection of probes. The array may comprise between 8 and 80 probes for each SNP. In one embodiment the collection comprises about 56 probes for each SNP. In a preferred embodiment the collection comprises about 40 probes for each SNP, 20 for each allele. The probes may be present in sets of 8 probes that correspond to a PM probe for each of two alleles, a MM probe for each of 2 alleles, and the corresponding probes for the opposite strand. So for each allele there may be a perfect match, a perfect mismatch, an antisense match and an antisense mismatch probe. The polymorphic position may be the central position of the probe region, for example, the probe region may be 25 nucleotides and the polymorphic allele may be in the middle with 12 nucleotides on either side. In other probe sets the polymorphic position may be offset from the center. For example, the polymorphic position may be from 1 to 5 bases from the central position on either the 5' or 3' side of the probe. The interrogation position, which is changed in the mismatch probes, may remain at the center position. In one embodiment there are 56 probes for each SNP: the 8 probes corresponding to the polymorphic position at the center or 0 position and 8 probes for the polymorphic position at each of the following positions: −4, −2, −1, +1, +3 and +4 relative to the central or 0 position. In another embodiment 40 probes are used, 8 for the 0 position and 8 for each of 4 additional positions selected from: −4, −2, −1, +1, +3 and +4 relative to the central or 0 position. The probes sets used may vary depending on the SNP, for example, for one SNP the probes may be −4, −2, 0, +1 and +4 and for another SNP they may be −2, −1, 0, +1 and +4. Empirical data may be used to choose which probe sets to use on an array. In another embodiment 24 or 32 probes may be used for one or more SNPs.

In many embodiments pairs are present in perfect match and mismatch pairs, one probe in each pair being a perfect match to the target sequence and the other probe being identical to the perfect match probe except that the central base is a homo-mismatch. Mismatch probes provide a control for non-specific binding or cross-hybridization to a nucleic acid in the sample other than the target to which the probe is directed. Thus, mismatch probes indicate whether hybridization is or is not specific. For example, if the target is present, the perfect match probes should be consistently brighter than the mismatch probes because fluorescence intensity, or brightness, corresponds to binding affinity. (See e.g., U.S. Pat. No. 5,324,633, which is incorporated herein for all purposes.) Finally, the difference in intensity between the perfect match and the mismatch probe (I(PM)-I(MM)) provides a good measure of the concentration of the hybridized material. See PCT No. WO 98/11223, which is incorporated herein by reference for all purposes.

In another embodiment, the current invention provides a pool of sequences that may be used as probes. Methods for making probes are well known. See e.g., MOLECULAR CLONING A LABORATORY MANUAL, Sambrook and Russell Eds., CSLH Press, ($3^{rd}$ ed. 2001), which is hereby incorporated in its entirety by reference for all purposes. Sambrook describes a number of uses for nucleic acid probes of defined sequence. Some of the uses described by Sambrook include: (1) screening cDNA or genomic DNA libraries, or subclones derived from them, for additional clones containing segments of DNA that have been isolated and previously sequenced; (2) identifying or detect the sequences of specific genes; (3) detecting specific mutations in genes of known sequence; to detect specific mutations generated by site-directed mutagenesis of cloned genes; (4) and mapping the 5' termini of mRNA molecules by primer extensions. Sambrook describes other uses for probes throughout. See also Alberts et al., MOLECULAR BIOLOGY OF THE CELL ($3^{rd}$ ed. 1994) at 307 and Lodish et al., MOLECULAR CELL BIOLOGY, ($4^{th}$ ed. 2000) at 285-286, each of which is hereby incorporated by reference in its entirety for all purposes, for a brief discussion of the use of nucleic acid probes in in situ hybridization. Other uses for probes derived from the sequences disclosed in this invention will be readily apparent to those of skill in the art. See e.g., Lodish et al., MOLECULAR CELL BIOLOGY, ($3^{rd}$ ed. 1995) at 229-233, incorporated above, for a description of the construction of genomic libraries.

In another embodiment, the current invention may be combined with known methods to genotype polymorphism in a wide variety of contexts. For example, the methods may be used to do association studies, identify candidate genes associated with a phenotype, genotype SNPs in clinical populations, or correlate genotype information to clinical phenotypes. The SNPs of Table 1 have been selected based on a number of criteria that make them suitable for complex genetic analysis, for example, linkage analysis and association studies. The SNPs of Table 1 are spaced throughout the genome at an average distance of 210 Kb from one another and they are known to be polymorphic in multiple populations. The panel of SNPs or a subset of these SNPs may be genotyped by any method available. See, Color Atlas of Genetics ($2^{nd}$ ed), Ed. Passarge (2001) Thieme, NY, N.Y., which is incorporated by reference.

For a discussion of genotyping analysis methods see, for example, Elena and Lenski Nature Reviews, Genetics 4:457469 (2003), Twyman and Primrose, Pharmacogenomics 4:67-79 (2003), Hirschhorn et al. Genetics in Medicine 4:45-61 (2002) and Glazier et al. *Science* 298:2345-2349 (2002) each of which is incorporated herein by references for all purposes. For a discussion of high throughput genotyping approaches see, for example, Jenkins and Gibson, *Comp Funct Genom* 2002; 3:57-66 which is incorporated herein by reference. For a review of methods of haplotype analysis in population genetics and association studies see, for example, Zhao et al. Pharmacogenomics 4:171-178 (2003), which is incorporated herein by reference.

One skilled in the art will appreciate that a wide range of applications will be available using 2 or more, 10 or more, 100 or more, 1000 or more, 10,000 or more, 100,000 or more, or more of the SEQ ID NOS 1-124,031 sequences as probes for polymorphism detection and analysis. The combination of the DNA array technology and the Human SNP specific probes in this disclosure is a powerful tool for genotyping and mapping disease loci.

In many embodiments the target sequences are a subset that is representative of a larger set. For example, the target sequences may be 1,000, 5,000, 10,000 or 100,000 to 10,000, 20,000, 100,000, 1,500,000 or 3,000,000 SNPs that may be representative of a larger population of SNPs present in a population of individuals. The target sequences may be dispersed throughout a genome, including for example, sequences from each chromosome, or each arm of each chromosome. Target sequences may be representative of haplotypes or particular phenotypes or collections of phenotypes. For a description of haplotypes see, for example, Gabriel et al., Science, 296:2225-9 (2002), Daly et al. Nat Genet., 29:229-32 (2001) and Rioux et al., Nat Genet., 29:223-8 (2001), each of which is incorporated herein by reference in its entirety.

In another embodiment, the present invention may be used for cross-species comparisons. One skilled in the art will appreciate that it is often useful to determine whether a SNP present in one species, for example human, is present in a conserved format in another species, including, without limitation, gorilla, chimp, mouse, rat, chicken, zebrafish, *Drosophila*, or yeast. See e.g. Andersson et al., *Mamm. Genome,* 7(10):717-734 (1996), which is hereby incorporated by reference for all purposes, which describes the utility of cross-species comparisons. The use of 2 or more, 10 or more, 100 or more, 1000 or more, 10,000 or more, 100,000 or more of the sequences disclosed in this invention in an array can be used to determine whether any sequence from one or more of the Human genes represented by the sequences disclosed in this invention is conserved in another species by, for example, hybridizing genomic nucleic acid samples from another species to an array comprised of the sequences disclosed in this invention.

In another embodiment of the invention, the sequences of this invention may be used to generate primers directed to their corresponding genes as disclosed in the GenBank or any other public database. The sequences provided in the sequence listing and the reference numbers provided in Table 1 may be used to identify the region of the genome containing the associated SNP. Primers may be used in such basic techniques as sequencing or PCR, see e.g., Sambrook, incorporated by reference above. In one embodiment PCR is allele specific.

In a preferred embodiment, the hybridized nucleic acids are detected by detecting one or more labels attached to the sample nucleic acids. The labels may be incorporated by any of a number of means well known to those of skill in the art. In one embodiment, the label is simultaneously incorporated during the amplification step in the preparation of the sample nucleic acids. Thus, for example, polymerase chain reaction (PCR) with labeled primers or labeled nucleotides will provide a labeled amplification product. In another embodiment, transcription amplification using a labeled nucleotide (e.g. fluorescein-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example, nick translation or end-labeling (e.g. with a labeled RNA) by kinasing the nucleic acid and subsequent attachment (ligation) of a nucleic acid linker joining the sample nucleic acid to a label (e.g., a fluorophore). In another embodiment label is added to the end of fragments using terminal deoxytransferase (TdT).

Detectable labels suitable for use in the present invention include any composition detectable by spectroscopic, photochemical, biochemical, immunochemical, electrical, optical or chemical means. Useful labels in the present invention include, but are not limited to: biotin for staining with labeled streptavidin conjugate; anti-biotin antibodies, magnetic beads (e.g., Dynabeads™); fluorescent dyes (e.g., fluorescein, texas red, rhodamine, green fluorescent protein, and the like); radiolabels (e.g., $^3H$, $^{125}I$, $^{35}S$, $^{14}C$, or $^{32}P$); phosphorescent labels; enzymes (e.g., horse radish peroxidase, alkaline phosphatase and others commonly used in an ELISA); and calorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241, each of which is hereby incorporated by reference in its entirety for all purposes.

Means of detecting such labels are well known to those of skill in the art. Thus, for example, radiolabels may be detected using photographic film or scintillation counters; fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

The label may be added to the target nucleic acid(s) prior to, or after the hybridization. So called "direct labels" are detectable labels that are directly attached to or incorporated into the target nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids. See Tijssen, LABORATORY TECHNIQUES IN BIOCHEMISTRY AND MOLECULAR BIOLOGY, VOL. 24: HYBRIDIZATION WITH NUCLEIC ACID PROBES (1993) which is hereby incorporated by reference in its entirety for all purposes.

D. Methods of Use

The methods of the presently claimed invention can be used for a wide variety of applications including, for example, linkage and association studies, identification of candidate gene regions, genotyping clinical populations, correlation of genotype information to phenotype information, loss of heterozygosity analysis, and identification of the source of an organism or sample, or the population from which an organism or sample originates. Any analysis of genomic DNA may be benefited by a reproducible method of polymorphism analysis.

Furthermore, the probes, sequences, arrays and collections of SNPs of the presently claimed invention are particularly well suited for study and characterization of extremely large regions of genomic DNA in individual samples and in populations.

In a preferred embodiment, the methods of the presently claimed invention are used to genotype individuals, populations or samples. For example, any of the procedures described above, alone or in combination, could be used to interrogate SNPs present in Table 1. The disclosed arrays could be used in conjunction with methods of reducing the complexity of a sample in a reproducible and predictable manner. For example, complexity reduction methods may be designed to amplify a collection of target sequences that correspond to fragments containing SNPs from Table 1. Arrays may be designed and manufactured on a large scale basis to interrogate those fragments with probes comprising sequences from SEQ ID NOS 1-124,031. Thereafter, a sample from one or more individuals would be obtained and prepared using the same techniques which were used to prepare the selection probes or to design the array. Each sample can then be hybridized to an array and the hybridization pattern can be analyzed to determine the genotype of each individual or a population of individuals. Methods of use for polymorphisms and SNP discovery can be found in, for example, U.S. Pat. No. 6,361,947 which is herein incorporated by reference in its entirety for all purposes.

Correlation of Polymorphisms with Phenotypic Traits

Most human sequence variation is attributable to or correlated with SNPs, with the rest attributable to insertions or deletions of one or more bases, repeat length polymorphisms and rearrangements. On average, SNPs occur every 1,000-2,000 bases when two human chromosomes are compared, resulting in an estimated 3,000,000 SNPs in the human genome. (See, The International SNP Map Working Group, Science 409: 928-933 (2001) incorporated herein by reference in its entirety for all purposes.) Human diversity is limited not only by the number of SNPs occurring in the genome but further by the observation that specific combinations of alleles are found at closely linked sites, generating haplotypes. For a description of haplotypes see, for example, Gabriel et al., Science, 296:2225-9 (2002), Daly et al. Nat Genet., 29:229-32 (2001) and Rioux et al., Nat Genet., 29:223-8 (2001), each of which is incorporated herein by reference in its entirety.

Correlation of individual polymorphisms or groups of polymorphisms with phenotypic characteristics is a valuable tool in the effort to identify DNA variation that contributes to population variation in phenotypic traits. Phenotypic traits include, for example, physical characteristics, risk for disease, and response to the environment. Polymorphisms that correlate with disease are particularly interesting because they represent mechanisms to accurately diagnose disease and targets for drug treatment. Hundreds of human diseases have already been correlated with individual polymorphisms but there are many diseases that are known to have an, as yet unidentified, genetic component and many diseases for which a component is or may be genetic. Large scale association studies using large groups of SNPs provides additional tools for disease association studies.

Many diseases may correlate with multiple genetic changes making identification of the polymorphisms associated with a given disease more difficult. One approach to overcome this difficulty is to systematically explore the limited set of common gene variants for association with disease.

To identify correlation between one or more alleles and one or more phenotypic traits, individuals are tested for the presence or absence of polymorphic markers or marker sets and for the phenotypic trait or traits of interest. The presence or absence of a set of polymorphisms is compared for individuals who exhibit a particular trait and individuals who exhibit lack of the particular trait to determine if the presence or absence of a particular allele is associated with the trait of interest. For example, it might be found that the presence of allele A1 at polymorphism A correlates with heart disease. As an example of a correlation between a phenotypic trait and more than one polymorphism, it might be found that allele A1 at polymorphism A and allele B1 at polymorphism B correlate with a phenotypic trait of interest.

Diagnosis of Disease and Predisposition to Disease

Markers or groups of markers that correlate with the symptoms or occurrence of disease can be used to diagnose disease or predisposition to disease without regard to phenotypic manifestation. To diagnose disease or predisposition to disease, individuals are tested for the presence or absence of polymorphic markers or marker sets that correlate with one or more diseases. If, for example, the presence of allele A1 at polymorphism A correlates with coronary artery disease then individuals with allele A1 at polymorphism A may be at an increased risk for the condition.

Individuals can be tested before symptoms of the disease develop. Infants, for example, can be tested for genetic diseases such as phenylketonuria at birth. Individuals of any age could be tested to determine risk profiles for the occurrence of future disease. Often early diagnosis can lead to more effective treatment and prevention of disease through dietary, behavior or pharmaceutical interventions. Individuals can also be tested to determine carrier status for genetic disorders. Potential parents can use this information to make family planning decisions.

Individuals who develop symptoms of disease that are consistent with more than one diagnosis can be tested to make a more accurate diagnosis. If, for example, symptom S is consistent with diseases X, Y or Z but allele A1 at polymorphism A correlates with disease X but not with diseases Y or Z an individual with symptom S is tested for the presence or absence of allele A1 at polymorphism A. Presence of allele A1 at polymorphism A is consistent with a diagnosis of disease X. Genetic expression information discovered through the use of arrays has been used to determine the specific type of cancer a particular patient has. (See, Golub et al. Science 286: 531-537 (2001) hereby incorporated by reference in its entirety for all purposes.)

Pharmacogenomics

Pharmacogenomics refers to the study of how genes affect response to drugs. There is great heterogeneity in the way individuals respond to medications, in terms of both host toxicity and treatment efficacy. There are many causes of this variability, including: severity of the disease being treated; drug interactions; and the individuals age and nutritional status. Despite the importance of these clinical variables, inherited differences in the form of genetic polymorphisms can have an even greater influence on the efficacy and toxicity of medications. Genetic polymorphisms in drug-metabolizing enzymes, transporters, receptors, and other drug targets have been linked to interindividual differences in the efficacy and toxicity of many medications. (See, Evans and Relling, Science 286: 487-491 (2001) which is herein incorporated by reference for all purposes).

An individual patient has an inherited ability to metabolize, eliminate and respond to specific drugs. Correlation of polymorphisms with pharmacogenomic traits identifies those polymorphisms that impact drug toxicity and treatment efficacy. This information can be used by doctors to determine what course of medicine is best for a particular patient and by pharmaceutical companies to develop new drugs that target a particular disease or particular individuals within the population, while decreasing the likelihood of adverse affects. Drugs can be targeted to groups of individuals who carry a specific allele or group of alleles. For example, individuals who carry allele A1 at polymorphism A may respond best to medication X while individuals who carry allele A2 respond best to medication Y. A trait may be the result of a single polymorphism but will often be determined by the interplay of several genes.

In addition some drugs that are highly effective for a large percentage of the population, prove dangerous or even lethal for a very small percentage of the population. These drugs typically are not available to anyone. Pharmacogenomics can be used to correlate a specific genotype with an adverse drug response. If pharmaceutical companies and physicians can accurately identify those patients who would suffer adverse responses to a particular drug, the drug can be made available on a limited basis to those who would benefit from the drug.

Similarly, some medications may be highly effective for only a very small percentage of the population while proving only slightly effective or even ineffective to a large percentage of patients. Pharmacogenomics allows pharamaceutical companies to predict which patients would be the ideal candidate for a particular drug, thereby dramatically reducing failure rates and providing greater incentive to companies to continue to conduct research into those drugs.

Determination of Relatedness

There are many circumstances where relatedness between individuals is the subject of genotype analysis and the present invention can be applied to these procedures.

Paternity testing is commonly used to establish a biological relationship between a child and the putative parent or relative of that child. Genetic material from the child can be analyzed for occurrence of polymorphisms and compared to a similar analysis of the putative father's genetic material. Determination of relatedness is not limited to the relationship between father and child but can also be done to determine the relatedness between mother and child, (see e.g. Staub et al., U.S. Pat. No. 6,187,540) or more broadly, to determine how related one individual is to another, for example, between races or species or between individuals from geographically separated populations, (see for example H. Kaessmann, et al. Nature Genet. 22, 78 (1999)). The SNPs of Table 1 may be used for paternity analysis in groups of 100 or more, 1000 or more or 10,000 or more. The SNPs may be used for anthropological studies.

Forensics

The capacity to identify a distinguishing or unique set of forensic markers in an individual is useful for forensic analysis. For example, one can determine whether a blood sample from a suspect matches a blood or other tissue sample from a crime scene by determining whether the set of polymorphic forms occupying selected polymorphic sites is the same in the suspect and the sample. If the set of polymorphic markers does not match between a suspect and a sample, it can be concluded (barring experimental error) that the suspect was not the source of the sample. If the set of markers does match, one can conclude that the DNA from the suspect is consistent with that found at the crime scene. If frequencies of the polymorphic forms at the loci tested have been determined (e.g., by analysis of a suitable population of individuals), one can perform a statistical analysis to determine the probability that a match of suspect and crime scene sample would occur by chance. A similar comparison of markers can be used to identify an individual's remains. For example the U.S. armed forces collect and archive a tissue sample for each service member. If unidentified human remains are suspected to be those of an individual a sample from the remains can be analyzed for markers and compared to the markers present in the tissue sample initially collected from that individual. The disclosed arrays, probes and SNPs may be used for forensic analysis.

Allele Frequency Determination

Large numbers of individuals, for example, 20, 40, 60, 100, 1000, 10,000, Or 100,000 or more may be genotyped at a particular SNP to determine the frequency of each of the possible alleles. Results from different populations may be compared to determine if some alleles are present at higher or lower frequencies in distinct populations. Some SNPs may be identified that are monomorphic (zero-heterozygosity) in one population but not in another population. Allele frequencies may be used to study phenomenon such as natural selection, random genetic drift, demographic evens such as population bottlenecks or expansions or combinations of these.

Genetic Mapping

The SNPs and arrays disclosed may be used to generate information useful for genetic mapping.

EXAMPLE

The following example serves to illustrate the type of experiment that could be conducted using the invention.

Polymorphism Detection by Hybridization to High Density Oligonucleotide Arrays

Arrays containing the desired number of probes can be synthesized using the method described in U.S. Pat. No. 5,143,854, incorporated by reference above. Nucleic acid may be amplified so that a collection of target sequences is preferentially amplified. The amplified fragments may be fragmented and end labeled with terminal deoxytransferase and biotin labeled nucleotides. Hybridizations are carried out in a flow cell that contains the two-dimensional DNA probe arrays. Following a brief washing step to remove unhybridized RNA, the arrays are scanned using a scanning confocal microscope.

Genomic DNA was digested with XbaI by mixing 5 µl 50 ng/µl human genomic DNA (Coriell Cell Repositories) with 10.5 µl H$_2$O (Accugene), 2 µl 10×RE buffer 2 (NEB, Beverly, Mass.), 2 µl 10×BSA (NEB, Beverly, Mass.), and 0.5 µl XbaI (NEB, Beverly, Mass.). The reaction was incubated at 30° C. for 2 hours, then the enzyme was inactivated by incubation at 70° C. for 20 min and then to 4° C. The reaction may be stored at −20° C.

For ligation of the adapters the digested DNA was then mixed with 1.25 µl 5 µM adaptor in TE pH 8.0, 2.5 µl T4 DNA ligation buffer and 1.25 µl T4 DNA Ligase (NEB, Beverly, Mass.) which is added last. The reaction was incubated at 16° C. for 2 hours then at 70° C. for 20 min and then to 4° C. The 25 µl ligation mixture is then diluted with 75 µl H$_2$O and may be stored at −20° C.

For PCR 10 µl of the diluted ligated DNA is mixed with 10 µl PCR buffer II (Perkin Elmer, Boston, Mass.), 10 µl 2.5 mM dNTP (PanVera Takara, Madison, Wis.), 10 µl 25 mM MgCl$_2$, 7.5 µl 10 µM primer (for a final concentration of 0.75 µM), 2 µl 5 U/µl Taq Gold (Perkin Elmer, Boston, Mass.) and 50.5 µl H$_2$O. For each array four 100 µl reactions were prepared. Amplification was done using the following program: 95° C. for 3 min; 35 cycles of 95° C. for 20 sec, 59° C. for 15 sec and 72° C. for 15 sec; and a final incubation at 72° C. for 7 min. The reactions were then held at 4° C. The lid heating option was selected.

The PCR reactions were then purified by mixing the 100 µl PCR reaction with 500 µl PB or PM buffer into Qiagen columns (Valencia, Calif.) and the column was centrifuged at 13,000 rpm for 1 min. Flow through was discarded and 750 µl PE buffer with ethanol was added into the column to wash the sample and the column was spun at 13,000 rpm for 1 min. The flow through was discarded and the column was spun at 13,000 rpm for another 1 min. The flow through was discarded and the column was placed in a new collection tube. For 2 of the 4 samples 30 µl of EB elution buffer pH 8.5 was added to the center of the QIAquick membrane to elute the sample and the columns were allowed to stand at room temperature for 5 min and then centrifuged at 13,000 for 1 min. The elution buffer from the first 2 samples was then used to elute the other 2 samples and the eluates were combined. The DNA was quantified and diluted so that 48 µl contains 20 µg DNA.

The DNA was fragmented by mixing 48 µl DNA (20 µg), 5 µl RE Buffer 4, and 2 µl 0.09 U/µl DNase in a total volume of 55 µl. The reaction was incubated at 37° C. for 30 min then 95° C. for 15 min and then held at 4° C.

Fragments were labeled by incubating 50 µl fragmented DNA, 13 µl 5×TdT buffer (Promega, Madison, Wis.), 1 µl 1 mM biotinolated-ddATP (NEN Life Sciences, Boston, Mass.), and 1 µl TdT (Promega, Madison, Wis.) at 37° C. overnight then at 95° C. for 10 min, then held at 4° C.

Hybridization mix is 12 µl 1.22 M MES, 13 µl DMSO, 13 µl 50× Denharts, 3 µl 0.5M EDTA, 3 µl 10 mg/ml herring sperm DNA, 3 µl 10 nM oligo B2, 3 µl 1 mg/ml Human Cot-1, 3 µl 1% Tween-20, and 140 µl 5M TMACL. 70 µl labeled DNA was mixed with 190 µl hybridization mix. The mixture was incubated at 95° C. for 10 min, spun briefly and held at 47.5° C. 200 µl of the denatured mixture was hybridized to an array at 47.5° C. for 16 to 18 hours at 60 rpm. The array comprised SEQ ID NOS. 1-124,031 tiled on an array along with mismatch, antisense match and antisense mismatch probes for each of the sequences. Each probe is present in a spatially addressable location.

Staining mix was 990 µl $H_2O$, 450 µl 20×SSPE, 15 µl Tween-20, 30 µl 50% Denharts. For the first stain mix 495 µl staining mix with 5 µl 1 mg/ml streptavidin (Pierce Scientific, Rockford, Ill.), for the second stain mix 495 µl staining mix with 5 µl 0.5 mg/ml biotinylated anti-streptavidin antibody (Vector Labs, Burlingame, Calif.) and for the third stain mix 495 µl staining mix with 5 µl 1 mg/ml streptavidin, R-phycoerythrin conjugate (Molecular Probes, Eugene, Oreg.). Wash and stain under standard conditions.

Hybridized samples were analyzed with a computer system to determine which alleles were present for a particular SNP.

CONCLUSION

The inventions herein provide a pool of unique nucleic acid sequences, which may be used to genotype a collection of Human SNPs. These sequences can be used for a variety of types of analyses.

The above description is illustrative and not restrictive. Many variations of the invention will become apparent to those of skill in the art upon review of this disclosure. The scope of the invention should, therefore, be determined not with reference to the above description, but instead be determined with reference to the appended claims along with their full scope of equivalents.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07300788B2). An electronic copy of the "Sequence Listing" will also be available from the USPTO upon request and payment of the fee set forth in 37 CFR 1.19(b)(3).

What is claimed is:

1. An array consisting of a plurality of nucleic acid probes, wherein each probe in the plurality of nucleic acid probes consists of one of the sequences listed in SEQ ID Nos. 1-124,031 and wherein the plurality of nucleic acid probes of the array consists of each of the sequences listed in SEQ ID NOS. 1-124,031.

2. An array consisting of a plurality of nucleic acid probes, wherein each probe in the plurality of nucleic acid probes consists of one of the sequences listed in SEQ ID NOS. 1-124,031 or the complement of one of the sequences listed in SEQ ID NOS: 1-124,031 and wherein the plurality of nucleic acid probes consists of each of the sequences listed in SEQ ID NOS. 1-124,031 and the complement of each of the sequences listed in SEQ ID NOS: 1-124,031.

3. An array consisting of a plurality of nucleic acid probes attached to a support, wherein each probe in the plurality of nucleic acid probes consists of one of the sequences listed in SEQ ID NOS. 1-124,031 or the sequence of one of the sequences listed in SEQ ID NOS: 1-124,031 except with a mismatch at the central position and wherein the plurality of nucleic acid probes consists of each of the sequences listed in SEQ ID NOS. 1-124,031 and each of the sequences listed in SEQ ID NOS. 1-124,031 with a mismatch at the central position.

4. An array consisting of a plurality of nucleic acid probes, wherein each probe in the plurality of nucleic acid probes consists of one of the sequences listed in SEQ ID Nos. 1-124,031, wherein the plurality of nucleic acid probes of the array consists of each of the sequences listed in SEQ ID NOS. 1-124,031 and wherein each probe is attached to a bead.

* * * * *